United States Patent [19]

Groves et al.

[11] 4,032,656

[45] June 28, 1977

[54] AROMATIC PROSTAGLANDIN DERIVATIVES

[75] Inventors: William G. Groves, Blue Bell; Bernard Loev, Broomall; Carl D. Perchonock, Philadelphia, all of Pa.

[73] Assignee: SmithKline Corporation, Philadelphia, Pa.

[22] Filed: Nov. 21, 1975

[21] Appl. No.: 634,094

[52] U.S. Cl. .......................... 424/308; 260/465 F; 260/473 A; 260/476 R; 260/521 R; 424/317
[51] Int. Cl.$^2$ ....................................... C07C 69/76
[58] Field of Search ....... 260/473 R, 473 A, 521 R; 424/308, 317

[56] References Cited

UNITED STATES PATENTS

| | | | |
|---|---|---|---|
| 3,804,883 | 4/1974 | Galantay | 260/473 R |
| 3,819,694 | 6/1974 | Galantay | 260/521 R |
| 3,824,278 | 6/1974 | Galantay | 260/521 R |

*Primary Examiner*—Paul J. Killos
*Attorney, Agent, or Firm*—Joseph A. Marlino; Richard D. Foggio; William H. Edgerton

[57] ABSTRACT

Aromatic prostaglandin derivatives are prepared. These compounds have valuable antiprostaglandin activity specifically inhibiting prostaglandin synthesis and antagonizing diarrhea induced by prostaglandin $E_2$(-$PGE_2$).

2 Claims, No Drawings

AROMATIC PROSTAGLANDIN DERIVATIVES

This invention relates to novel aromatic prostaglandin derivatives having valuable antiprostaglandin activity. More specifically, the compounds of this invention inhibit prostaglandin synthesis and antagonize diarrhea induced by $PGE_2$.

There have been strong indications that the anti-inflammatory activity of non-steroidal compounds such as aspirin, indomethacin, and phenylbutazone was due to their ability to inhibit the synthesis of prostaglandins (Nature New Biology, Vol. 231, June 23, 1971). The inhibition of prostaglandin synthesis is considered by many skilled in the art to perhaps be the mechanism underlying other therapeutic actions of aspirin- and indomethacin-like compounds.

It is therefore the object of the present invention to provide novel aromatic prostaglandin derivatives which display the above-mentioned prostaglandin antagonism and which may lend themselves as anti-inflammatory agents.

The compounds of this invention are represented by the following structural formula:

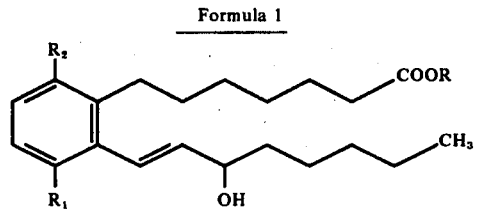

Formula 1 in which:

R represents hydrogen or lower alkyl of from 1–3 carbon atoms; and $R_1$ and $R_2$ represent hydrogen or lower alkoxy of from 1–3 carbon atoms.

Advantageously compounds of this invention are represented by the above structural formula when R represents hydrogen, and $R_1$ and $R_2$ represent hydrogen and methoxy.

Aromatic prostaglandin analogs with the aromatic ring being a 2,4 substituted dimethoxy benzene are disclosed in Belgium Pat. No. 774,784. These analogs do not possess the side chains present in the natural prostaglandins and are useful as fertility control agents, abortifacients, hypotensives, and bronchodilators.

The compounds of this invention may also be used in the form of metallic salts, such as, for example, alkali metal, or ammonium salts.

The compounds of Formula 1 are prepared according to the following sequence of reactions:

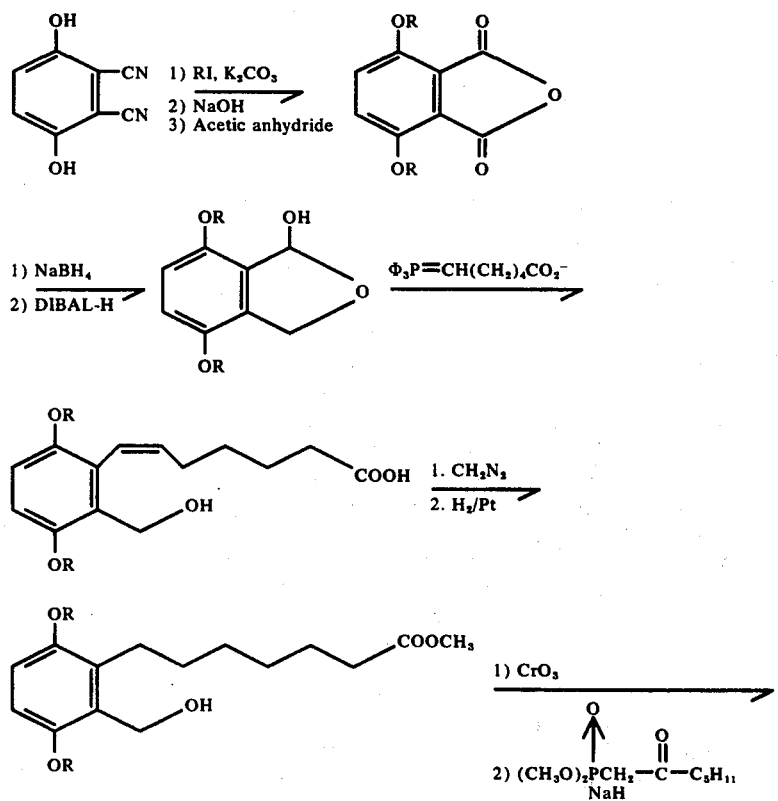

Scheme I

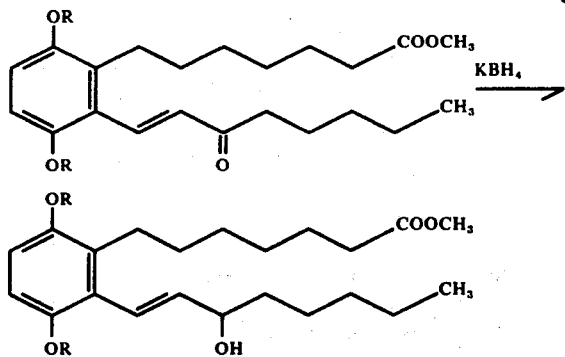

Scheme II

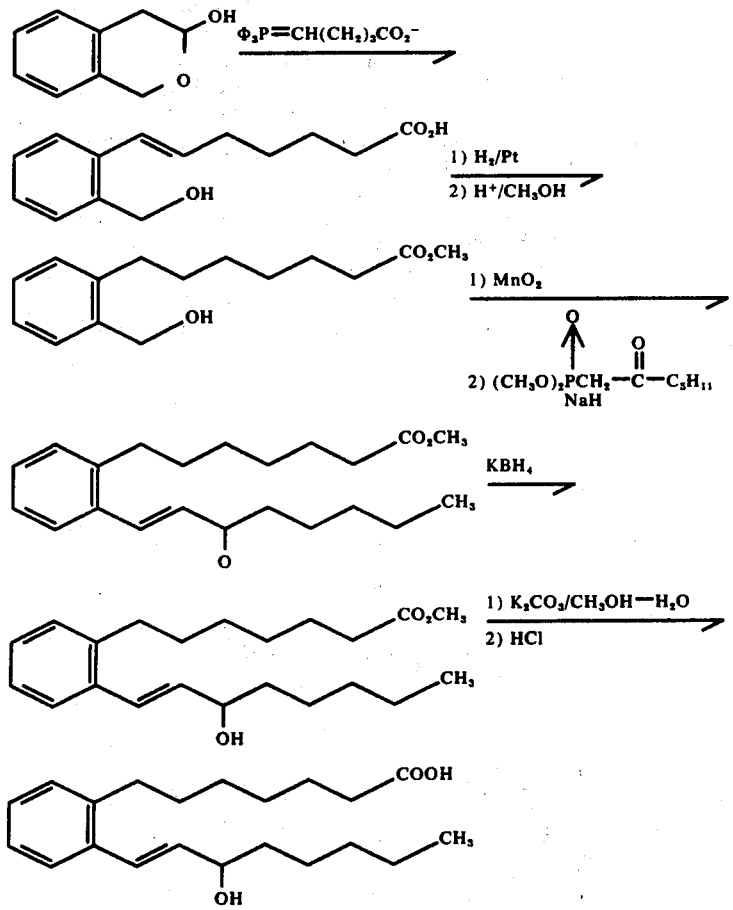

These reactions are carried out using readily available materials and give good yields of the end product. Thus, as shown above for the 1,4 di-substituted benzenes, dicyanohydroquinone is sequentially treated with the appropriate alkyl halide, sodium hydroxide, and acetic anhydride, to yield the corresponding phthalic anhydride, which is then reduced to the isobenzofuranol derivative. The latter is treated with the ylide derived from 5-carboxy-pentyltriphenylphosphonium bromide to give the cis-heptenoic acid. This derivative is esterified and hydrogenated to produce the corresponding saturated hydroxy ester. The ester is then oxidized and treated with the sodium salt of dimethyl(2-oxoheptyl)phosphonate to yield the enone. The enone compound is then reduced to the corresponding alcohol by reacting it with a suitable reducing agent such as potassium borohydride in a suitable organic solvent. The ester is converted to the acid by reacting it with an aqueous alcoholic potassium carbonate solution.

The preparation of the benzene derivatives which are not substituted at the 1,4 position is outlined in Scheme II. As shown above, 3-hydroxyisochroman is employed as a starting material and a similar procedure as disclosed in Scheme I is followed.

Further the compound of this invention contains an asymmetric carbon atom. Thus, it exists as d and l isomers. Unless otherwise specified in the description and accompanying claims, it is intended to include all isomers, whether separated or mixtures thereof.

The compounds of this invention have been demonstrated to inhibit prostaglandin synthesis and antagonize diarrhea induced by $PGE_2$ by employing modified standard test procedures. The prostaglandin synthesis inhibition method as employed is reported by Takeguchi and Sih, Prostaglandins, 2, 169, 1972. The principle entails the arachidonic acid-dependent formation of adrenochrome from L-epinephrine during prostaglandin biosynthesis. Indomethacin, phenylbutazone and aspirin were used as reference compounds.

A preferred compound of this invention 1-(6-carboxyhexyl)-2-(3-hydroxy-trans-1-octenyl)-benzene demonstrated a 100% inhibition of prostaglandin synthesis at 1000 $\mu M$ and has an $ID_{50}$ of 410 $\mu M$. This is twice as potent an inhibitor as phenylbutazone and nine times as potent as aspirin which have $ID_{50}$'s of 875 $\mu M$ and 3700 $\mu M$ respectively.

The antagonism of diarrhea induced by prostaglandin $E_2$ ($PGE_2$) was determined by employing the modified standard animal pharmacological test procedure as reported in Intra Science Chem. Rept, 6:1–9, 1972 and Annals of the New York Academy of Sciences, 180:386–95, 1971. Briefly the test comprises administering the test compounds subcutaneously 15 minutes prior to an intraperitoneal injection of $PGE_2$. Each animal is examined for diarrhea (which results after the administration of $PGE_2$) every 15 minutes for one hour post-drug. Polyphloretin phosphate and 7 oxa-13-prostynoic acid, both well known antagonists of prostaglandin induced diarrhea, were employed as reference compounds.

An advantageous compound of this invention is 1-(6-carbomethoxyhexyl)-2-(3-hydroxy-trans-1-octenyl)-benzene which inhibits the $PGE_2$ diarrhea in mice by 53% at a dose of 20 mg./kg. as compared to a 36% inhibition with polyphloretin phosphate at the same dose.

The novel compounds of this invention may be administered orally or parenterally to an animal in conventional dosage unit forms such as tablets, capsules, injectables or the like by incorporating the appropriate dose of a compound of Formula 1 with carriers according to the accepted pharmaceutical practices. The aromatic prostaglandin derivatives will be present in an amount sufficient to produce anti-prostaglandin activity, Preferably the dosage unit forms will contain the compounds of Formula 1 in an amount of from about 10 to about 1000 mg., advantageously from about 100 to about 500 mg. Most advantageously equal daily doses are administered one to four times daily to provide a daily dosage regimen of from about 10 to about 4000 mg.

The pharmaceutical carrier employed may be, for example, either a solid or liquid. Exemplary of solid carriers are lactose, terra alba, talc, sucrose, gelatin, agar, pectin, acacia, magnesium stearate, stearic acid, and the like. Exemplary of liquid carriers are syrup, peanut oil, olive oil, water and the like. Similarly, the carrier as diluent can include any time delay material well known to the art such as glyceryl monostearate or glyceryl distearate alone or with a wax.

A wide variety of pharmaceutical forms can be employed. Thus if a solid carrier is used the preparation can be tableted, placed in a hard gelatin capsule in powder or pellet form or in the form of a troche or lozenge. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampule, or an aqueous liquid suspension.

The following examples illustrate the preparation of specific compounds having antiprostaglandin activity. However, this should not be construed as a limitation of the invention since other variations will be obvious to those skilled in the art.

EXAMPLE 1

A mixture of 17.1 g. of 2,3-dicyanohydroquinone, 143.5 g. of methyl iodide and 43.5 g. of potassium carbonate is stirred in dimethylformide for approximately 20 hours. The mixture is then treated with 1 liter of water and filtered. The precipitate is washed with water and methanol and dried to yield 3,6-dimethoxyphthalonitrile. The nitrile is then slurried in 150 ml. of sodium hydroxide and heated at 115° C. for approximately 7 hours. The resulting solution is cooled, filtered and acidified with hydrochloric acid to precipitate 3,6-dimethoxyphthalic acid. The acid is refluxed in 150 ml. of acetic anhydride for 15 hours and then cooled to room temperature. The resulting crystals are filtered and washed with ether to yield 3,6-dimethoxyphthalic anhydride having a melting point of 265°–268° C.

To an ice-cold solution of 1.7 g. of sodium borohydride in 100 ml. of dimethylformide is added 9.2 g. of 3,6-dimethoxyphthalic anhydride. The cold bath is removed and the mixture stirred for 1 hour. The mixture is cooled in ice and 20 ml. of hydrochloric acid is slowly added. The solvent is removed in vacuo and the residue is slurried in 100 ml. of water. The resulting solid is filtered, dissolved in chloroform and dried. After removal of solvent, the solid is recrystallized from toluene to yield 4,7-dimethoxyphthalide with a melting point of 168°–170° C.

To a solution of 6.19 g. of 4,7-dimethoxyphthalide in 500 ml. of methylene chloride which is cooled to −60° C. is added 48 ml. of diisobutylaluminum hydride in toluene and the mixture is stirred for one hour, 5 ml. of methanol is added and the solution is allowed to come to ambient temperature. The mixture is then treated with 600 ml. of chloroform and 300 ml. of sodium chloride solution and filtered. The organic layer is dried and the solvent removed to yield a white solid. This is washed with hexane to yield 4,7-dimethoxy-1,3-dihydro-1-isobenzofuranol having a melting point of 156°–158° C.

To a solution of 22.8 g. of 5-carboxypentyltriphenylphosphonium bromide in 75 ml. of dimethylsulfoxide is added dropwise a solution of the sodium salt of dimethylsulfoxide. The solution is stirred, 3.15 g. of the above isobenzofuranol in 15 ml. of dimethylsulfoxide is added, and stirring is continued for approximately 70 hours. The mixture is poured into 450 ml. of ice water and filtered. The filtrate is extracted with ether-ethyl acetate (1:1) and the organic layer is extracted with sodium hydroxide. The combined aqueous fractions are acidified to pH2 and filtered. The filtrate is extracted with ether-pentane (2:1) and the extract is washed with water and dried. The solvent is removed to leave 1,4-dimethoxy-2-hydroxymethyl-3-(6-carboxy-cis-1-heptenyl)benzene which is dissolved in ether and esterified with diazomethane. The ester is dissolved in 100 ml. of ethanol, treated with activated charcoal and filtered. It is then hydrogenated at atmospheric pressure with 146 mg. of platinum oxide. The mixture is filtered to yield 1,4-dimethoxy-3-(6-carbomethoxyhexyl)-2-hydroxymethylbenzene.

To a solution of 1.6 g. of the latter in 75 ml. of acetone is added dropwise 1.9 g. of reagent (prepared from 10.3 g. chromium oxide, 30 ml. of water and 8.7 ml. of sulfuric acid) and the mixture is stirred for 10 minutes. 1 ml. of isopropyl alcohol is added and the system is brought to room temperature. The mixture is filtered and the filtrate is diluted with 100 ml. of brine and extracted with ether. The extracts are washed with sodium bicarbonate solution and dried. The solvent is removed to yield 2-(6-carbomethoxyhexyl)-3-formyl-1,4-dimethoxybenzene.

To a slurry of 278 mg. of a dispersion of sodium hydride in mineral oil in 40 ml. of dimethoxyethane is added a solution of 1.33 g. of dimethyl(2-oxoheptyl)phosphonate in 40 ml. of dimethoxyethane and the mixture is stirred for one hour. 1.41 g. of the aldehyde in 40 ml. of dimethoxyethane is added and the mixture heated at 85° C. for 18 hours. The mixture is then cooled and neutralized with acetic acid and the solvent is removed in vacuo. The residue is then chromatographed on a silica gel column to yield 1,4-dimethoxy-2-(6-carbomethoxyhexyl)-3-(3-oxo-trans-1-octenyl)-benzene as a yellow oil.

To a solution of the latter in 50 ml. of methanol is added 1.60 g. of potassium borohydride. The mixture is stirred for an hour, filtered, and the filtrate is cooled in ice and neutralized with acetic acid. The solvent is removed and the residue is dissolved in chloroform, washed with water and dried. The solvent is removed and the resulting oil is chromatographed to yield 1,4-dimethoxy-2-(6-carbomethoxyhexyl)-3-(3-hydroxy-trans-1-octenyl)benzene.

EXAMPLE 2

To a solution of 60.2 g. of 4-carboxybutyltriphenylphosphonium bromide in 200 ml. of dimethylsulfoxide is added a solution of the sodium salt of dimethylsulfoxide. The solution is stirred for one hour and 6.8 g. of 3-hydroxyisochromane in 25 ml. of dimethylsulfoxide is added. The solution is stirred at room temperature for 40 hours and then poured into 1200 ml. of ice water and filtered. The filtrate is washed with ether-ethyl acetate (1:1) and acidified to pH2 with oxalic acid. The mixture is again filtered and the filtrate with ether-pentane (2:1). The extract is washed with brine, dried, concentrated, and the solid recrystallized from toluene to yield 7-(2-hydroxymethylphenyl)trans-6-heptenoic acid as white crystals having a melting point of 92°-94.5° C.

A solution of 2.30 g. of the above heptenoic acid in 100 ml. of ethanol is stirred with 5 g. of activated charcoal for 30 minutes and filtered. The filtrate is hydrogenated at atmospheric pressure in the presence of 143 mg. of platinum oxide. The solution is filtered, evaporated and recrystallized from toluene to yield 2-(6-carboxyhexyl)benzyl alcohol as white crystals having a melting point of 75°-77° C.

A solution of 1.20 g. of this hydroxy-acid in 100 ml. of CH₃OH is refluxed for approximately 15 hours with 2.2 g. of AG 50-WX8 resin (benzene sulfonic acid bound to polystyrene). The solution is then filtered and the solvent is evaporated to yield 2-(6-carbomethoxyhexyl)benzyl alcohol.

A solution of 1.25 g. of this benzyl alcohol in 75 ml. of chloroform is added to a slurry of 12.5 g. of activated manganese dioxide in 75 ml. of chloroform. The mixture is stirred for 1 hour, filtered and the solvent is evaporated to leave 2-(6-carbomethoxyhexyl)benzaldehyde as a clear oil. To a slurry of 260 ml. of a dispersion of sodium hydride in mineral oil in 40 ml. of dimethoxyethane is addes a solution of 1.31 g. of dimethyl(2-oxoheptyl)phosphonate in 25 ml. of dimethoxyethane. The slurry is stirred for 1 hour, cooled to 0° C. and 1.22 g. of the benzaldehyde in 20 ml. of dimethoxyethane is added. The mixture is stirred at 0° for 30 minutes and at room temperature for 3 hours. It is then neutralized with acetic acid and the solvent removed in vacuo. The residue is chromatographed on silica gel to yield 1-(6-carbomethoxyhexyl)-2-(3-oxo-trans-1-octenyl)benzene as a pale yellow oil.

To a solution of 0.35 g. of the above oxo compound in 10 ml. of methanol is added 0.32 g. of potassium borohydride. The mixture is stirred for 1 hour, filtered, and the filtrate is cooled in ice and neutralized with acetic acid. The solvent is removed and the residue taken up in ether, washed with water and dried. The solvent is evaporated and the residue is chromatographed on silica gel to yield 1-(6-carbomethoxyhexyl)-2-(3-hydroxy-trans-1-octenyl)benzene as a pale yellow oil.

A solution of 1.28 g. of 1-(6-carbomethoxyhexyl)-2-(3-hydroxy-trans-1-octenyl)benzene in 150 ml. of methanol is cooled to 0° C. and a solution of 3.0 g. of potassium carbonate in 100 ml. of water is added. The ice bath is removed and the mixture is stirred for 24 hours. The methanol is removed in vacuo and the basic aqueous solution is washed with ether, cooled in ice and acidified to pH2 with dilute hydrochloric acid. The solution is then extracted with ether and the extract is washed with water and dried. The solvent is removed to yield 1-(6-carboxyhexyl)-2-(3-hydroxy-trans-1-octenyl)benzene.

Similarly employing 1,4-dimethoxy-2-(6-carbomethoxyhexyl)-3-(3-hydroxy-trans-1-octenyl)benzene and hydrolyzing as above with methanol and potassium carbonate yields 1,4-dimethoxy-2(6-carboxyhexyl)-3-(3-hydroxy-trans-1-octenyl)benzene.

EXAMPLE 3

| Ingredients | Mg./Capsule |
|---|---|
| 1-(6-carboxyhexyl)-2-(3hydroxy-trans-1-octenyl)benzene | 500 |
| Lactose | 50 |
| Starch | 50 |

All the ingredients are thoroughly mixed and placed in a hard gelatin capsule.

One capsule is taken three times a day.

What is claimed is:

1. A pharmaceutical composition in dosage unit form having antiprostaglandin activity comprising a chemical compound of the formula:

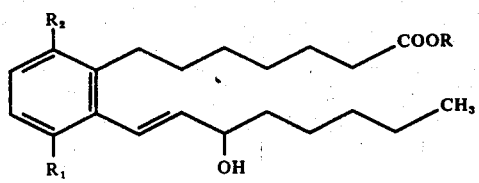

in which:

R is hydrogen or lower alkyl; and $R_1$ and $R_2$ are hydrogen or lower alkoxy of from 1 to 3 carbon atoms;
and a pharmaceutical carrier.

2. A method of producing antiprostaglandin activity which comprises administering internally to an animal a chemical compound as defined in claim 1 in an amount sufficient to produce said activity.

* * * * *